United States Patent
Mohamed et al.

(10) Patent No.: US 11,602,519 B1
(45) Date of Patent: Mar. 14, 2023

(54) METHOD FOR PREVENTING MYOCARDIAL INFARCTION USING EUCALYPTOL

(71) Applicant: KING FAISAL UNIVERSITY, Al-Ahsa (SA)

(72) Inventors: Maged Elsayed Mohamed, Al-Ahsa (SA); Bander Essa Aldhubiab, Al-Ahsa (SA); Nancy Safwat Abdeldaium Younis, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 17/465,832

(22) Filed: Sep. 2, 2021

(51) Int. Cl.
*A61K 31/352* (2006.01)
*A61P 9/10* (2006.01)

(52) U.S. Cl.
CPC .............. *A61K 31/352* (2013.01); *A61P 9/10* (2018.01)

(58) Field of Classification Search
CPC ............................... A61K 31/352; A61P 9/10
See application file for complete search history.

(56) References Cited

U.S. PATENT DOCUMENTS 9,278,081 B2   3/2016  Daley

FOREIGN PATENT DOCUMENTS

| CN | 102772741 A | 11/2012 |
| CN | 108379510 A | 8/2018 |
| KR | 2009-0132899 A | 12/2009 |

OTHER PUBLICATIONS

Bocsan et al., Molecules. Jun. 2021; 26(11): 3221 (Published online May 27, 2021) (Year: 2021).*
Shivashankara et al., Bioactive Food as Dietary Interventions for Liver and Gastrointestinal Disease, 2013 (Year: 2013).*
Kennedy-Feitosa et al., Phytomedicine, vol. 55, Mar. 1, 2019, pp. 70-79 (Year: 2019).*
Seol et al., Drug Discovery from Mother Nature, Advances in Experimental Medicine and Biology 929, 2016 (Year: 2016).*
Santos et al., Phytother Res. Jun. 2000;14(4):240-4. (Year: 2000).*
Soares et al., "Eucalyptol, an essential oil, reduces contractile activity in rat cardiac muscle," Brazilian Journal of Medical and Biological Research, Mar. 2005, vol. 38(3), pp. 453-461.
Lajis et al., "Therapeutic application of herbal essential oil and its bioactive compounds as complementary and alternative medicine in cardiovascular associated diseases," Insights on the Depression and Anxiety, Mar. 10, 2020.

* cited by examiner

*Primary Examiner* — Jean P Cornet
(74) *Attorney, Agent, or Firm* — Nath, Goldberg & Meyer; Richard C. Litman

(57) ABSTRACT

A method of treating or preventing myocardial infarction can include administering a therapeutically effective amount of eucalyptol (1,8-cineole) to a patient in need thereof. Eucalyptol can be a cardio-protective agent against myocardial infarction by decreasing inflammatory mediators and attenuating apoptosis of myocardial cells. Eucalyptol can inhibit the Toll-Like Receptors (TLRs) cascade, particularly via the TLR4/MyD88/NF-κB pathway, to prevent or lessen myocardial infarction-accompanied inflammation and apoptosis. Eucalyptol has a high therapeutic index, minor toxicity, and is well tolerated by the body.

6 Claims, 15 Drawing Sheets

Specification includes a Sequence Listing.

Eucalyptol/1,8-Cineolo/1,8-Epoxy-p-menthane

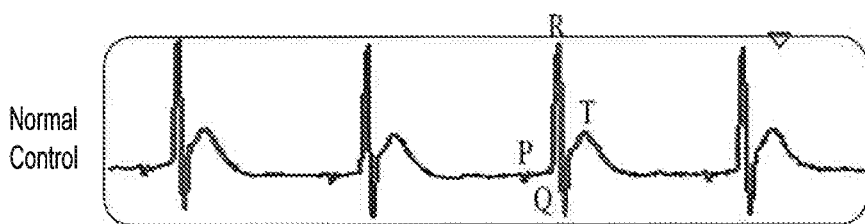
FIG. 2A  Normal Control
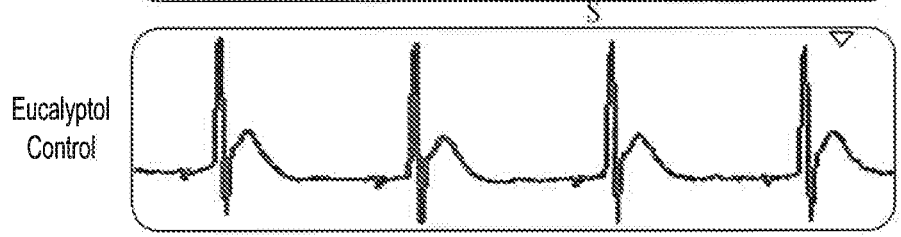
FIG. 2B  Eucalyptol Control
FIG. 2C  ISO Control
FIG. 2D  Eucalyptol Pretreatment

US 11,602,519 B1

METHOD FOR PREVENTING MYOCARDIAL INFARCTION USING EUCALYPTOL

INCORPORATION BY REFERENCE OF MATERIAL SUBMITTED IN COMPUTE READABLE FORM

The Applicants hereby incorporate by reference the sequence listing contained in the ASCII text filed titled 32087_29_Sequence_Listing_ST25.txt, created Mar. 2, 2021, and having 3 KB of data.

BACKGROUND

1. Field

The disclosure of the present patent application relates to a method of treating or preventing myocardial infarction, and particularly to a method for treating and preventing myocardial infarction using eucalyptol.

2. Description of the Related Art

Eucalyptol is a monoterpene epoxide in the essential oil of several *eucalyptus* species. Eucalyptol content in the essential oil fluctuates in the different *eucalyptus* species, from 25% to 90%. Eucalyptol has exhibited many pharmacological activities, including antibacterial and expectorant, anti-inflammatory, anti-hypertensive, and anti-cancer.

Myocardial infarction is a well-identified cardiovascular disease, characterized by the low supply of blood to the heart muscle, resulting in necrosis, damage or death to parts of the muscle, which could affect heart function and may lead to death. Current treatment for myocardial infraction (MI) has remarkably improved cardiac performance outcomes and patient survival rate, however; MI is still a main cause of death globally.

Thus, a method of treating or preventing myocardial infarction solving the afore-mentioned problems is desired.

SUMMARY

A method of treating or preventing myocardial infarction can include administering a therapeutically effective amount of eucalyptol (1,8-cineole) to a patient in need thereof. In an embodiment, the eucalyptol can be administered prior to myocardial infarction to a patient that is determined to be vulnerable to myocardial infarction. Eucalyptol can be a cardio-protective agent against myocardial infarction by decreasing inflammatory mediators and attenuating apoptosis of myocardial cells. Eucalyptol can inhibit the Toll-Like Receptors (TLRs) cascade, particularly via the TLR4/MyD88/NF-κB pathway, to prevent or lessen myocardial infarction-accompanied inflammation and apoptosis. Eucalyptol has a high therapeutic index, minor toxicity, and is well tolerated by the body.

These and other features of the present subject matter will become readily apparent upon further review of the following specification.

BRIEF DESCRIPTION OF THE DRAWINGS

FIGS. 2A-21) depict ECG demonstrative images from (A) normal control; (B) eucalyptol control; (C) ISO control; and (D) eucalyptol pretreatment experimental groups to illustrate the effect of pretreatment with eucalyptol (100 and 200 mg/kg) for 21 days on ECG components in ISO induced MI animals.

FIGS. 4A-41) are graphs showing the effect of pretreatment with eucalyptol (100 and 200 mg/kg) for 21 days on mRNA expression of (A) TLR2, (B) TLR4, (C) MYD88 and (D) TRIF in ISO induced MI animals. All values are stated as mean±SD (n=6). Probability value is $p<0.05$: where # indicates statistically significant from normal control group, ≠ indicates statistically significant from ISO induced MI group, * indicates statistically significant from Eucalyptol (100 mg/kg) group using one-way ANOVA followed by Tukey's test as a post-hoc analysis.

FIGS. 6A-61) are graphs showing the effect of pretreatment with eucalyptol (100 and 200 mg/kg) for 21 days on (A) IL-6, (B) NF-κB, (C) TNF-α and (D) HSP-60 in ISO induced MI animals. All values are stated as mean±SD (n=6). Probability value is $p<0.05$: where # indicates statistically significant from normal control group, ≠ indicates statistically significant from ISO induced MI group, * indicates statistically significant from Eucalyptol (100 mg/kg) group using one-way ANOVA followed by Tukey's test as a post-hoc analysis.

DETAILED DESCRIPTION OF THE PREFERRED EMBODIMENT

Figure 1A:
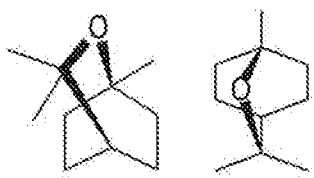
FIGS. 1A-1C depict (A) the structure of eucalyptol (1,8-Cineole or 1,8-Epoxy-p-menthane); (B) a graph showing the effect of pretreatment with eucalyptol (100 and 200 mg/kg) for 21 days on heart to body ratio in ISO induced MI animals; and (C) a graph showing the effect of pretreatment with eucalyptol (100 and 200 mg/kg) for 21 days on infarct size percentage in ISO induced MI animals. All values are stated as mean SD (n=6). Probability value is $p<0.05$: where # indicates statistically significant from normal control group, ≠ indicates statistically significant from ISO (isoproterenol)-induced MI group, using one-way ANOVA followed by Tukey's test as a post-hoc analysis. ISO: isoproterenol; TTC: triphenyl tetrazolium chloride.

A method of treating or preventing myocardial infarction (MI) can include administering a therapeutically effective amount of eucalyptol (1,8-cineole, 1,8 epoxy-p-methane) (FIG. 1A) to a patient in need thereof. The eucalyptol can be administered to the patient prior to myocardial infarction to provide a cardio-protective effect against myocardial infarction by preventing or inhibiting myocardial infarction-accompanied inflammation and apoptosis of myocardial cells. Eucalyptol has a high therapeutic index, minor toxicity, and is well tolerated by the body.

Throughout this application, the term "about" may be used to indicate that a value includes the standard deviation of error for the composition, device or method being employed to determine the value.

The use of the term "or" in the specification and claim(s) is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps. In certain cases, the term "comprising" may be replaced with "consisting essentially of" or "consisting of."

The use of the word "a" or "an" when used herein in conjunction with the term "comprising" in the claims and/or the specification may mean "one," but it is also consistent with the meaning of "one or more," "at least one," and "one or more than one."

The phrase "pharmaceutically acceptable," as used herein, refers to molecular entities and compositions that do not produce an allergic or similar untoward reaction when administered to a human.

The term "patient," as used herein, means a mammal, including but not limited to a human being.

As used herein, the term "providing" an agent is used to include "administering" the agent to a subject.

As used herein, a "carrier" includes any and all solvents, dispersion media, vehicles, coatings, diluents, isotonic and absorption delaying agents, buffers, carrier solutions, suspensions, colloids, excipients, and the like.

Necrotic cardiac myocytes release an extensive range of endogenous damage-associated molecular pattern molecules (DAMPs), such as heat shock protein (HSP), high mobility group box 1 (HMGB1), fibrinogen and others, which further prompt Toll-like Receptors (TLRs) as well as the innate immune system. DAMPs associate with TLRs to trigger downstream signaling as well as stimulate transcription factors, thus prompting inflammation. TLRs signal cascade could be separated into two pathways: myeloid differentiation protein 88 (MyD88) and TRIF pathways. TLR4 binding to ligands eventually triggers nuclear factor-kappa B (NF-κB) translocation with subsequent extensive inflammation response as well as immune associated gene expression. TLRs, particularly TLR2 and TLR4, play a significant role in the damaging effects occurring in ischemic injury accompanying myocardial infarction. Within the initial few minutes of injury, NF-κB translocate to the nucleus to prompt pro-inflammatory and proapoptotic gene expression, triggering cell dysfunction and death. Thus, TLR4/NF-κB signaling pathway plays a crucial part in myocardial injury.

It is believed that eucalyptol shields myocytes by inhibiting the TLR4/MyD88/NF-κB signaling pathway and, thereby, successfully recovers cardiac performance and ameliorates myocardial inflammation. As described herein, mRNA and protein expression of the TLR pathway were determined together with the subsequent inflammatory mediators and apoptotic markers. The results showed that eucalyptol diminished mRNA and protein expressions of TLR2, TLR4, MYD88 and TRIF, resulting in lessened post-myocardial infarction TLR pathway activity and, consequently, lessened myocardial infarction inflammatory mediators and apoptotic markers. For initiating a signaling cascade to activate NF-κB, DAMP bind to the TLR, leading to MyD88 recruitment, IKKs phosphorylation, IκBs phosphorylation and degradation, NF-κB translocation into the nucleus, and finally activation of downstream genes. Accordingly, the data presented herein demonstrates reduced TLR pathway activity and impaired translocation of NF-κB p65 into the nucleus.

As described herein, isoproterenol (ISO)-induced MI in mice resulted in significant increase in heart to body ratio, expanded infarcted region, intensification in numerous cardiac enzyme indicators and heart rate (HR) as well as numerous ECG alterations, suggesting infarcted myocardium manifestation. When mice were pretreated with eucalyptol, however, an infarcted restricting effect was observed, with diminishing cardiac indicator enzymes, diminishing stabilization of HR, and ECG adjustment. All of these actions establish the cardio-protective effects of eucalyptol in myocardial infarction.

As described herein, myocardial infarction induced in laboratory rats (Isoproterenol-rat model) resulted in a substantial increase in mRNA and protein expression of TLR2, TLR4 and their adaptor proteins MYD88 and TRIF as well as elevation in inflammatory and apoptotic (Bax, Caspase 3 and 9) markers, indicating the inflammatory and apoptotic consequences arising within the myocardium following myocardial infarction propagation. As demonstrated by the experiments described herein, administration of eucalyptol inhibited NF-κB expression, and decreased various inflammatory mediator levels.

Accordingly, eucalyptol can decrease inflammatory mediators and attenuate the apoptosis of myocardial cells after myocardial infarction through inhibition of TLR/NF-κB, resulting in decreased levels of pro-inflammatory NF-κB target genes.

An embodiment of the present subject matter is directed to a pharmaceutical composition comprising eucalyptol and a pharmaceutically acceptable carrier. The pharmaceutical composition can be prepared by mixing eucalyptol with a pharmaceutically acceptable carrier. For example, the method of making a pharmaceutical composition can include mixing eucalyptol under sterile conditions with a pharmaceutically acceptable carrier with preservatives, buffers, and/or propellants to create the pharmaceutical composition. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of eucalyptol or an amount effective to treat or prevent myocardial infarction may be determined initially from the Examples described herein and adjusted for specific targeted diseases using routine methods.

The present teachings are illustrated by the following examples.

EXAMPLES

Materials and Methods

Animals

Male Wister rats (weight: 250-270 g) were kept at standard laboratory conditions with free access to a pellet diet and tap water ad libitum throughout the experiment. All animal investigational protocols and practices were in accordance with the Ethical Conduct for Use of Animals in Research Guidelines in King Faisal University and were authorized by the Animal Research Ethics Committee at King Faisal University.

Animals were distributed into five groups randomly (n=6). The animals in normal and eucalyptol control groups were administered either saline or eucalyptol for 3 weeks and then saline (s.c) on the last two days of the experiment (20th and 21st days). The animals in the myocardial infarction (MI) control group were given saline orally for 3 weeks, then challenged with Isoproterenol (ISO) (85 mg/kg, s.c.) as stated before on the 20th and 21st days to induce MI. The animals in the eucalyptol pretreatment groups were pretreated with eucalyptol (either 100 or 200 mg/kg) orally for 3 weeks then confronted with ISO (85 mg/kg s.c.) on the last two days of the experiment. All experimental animals were killed 24 hrs after the second dose of ISO.

Electrocardiogram (ECG) Recording

At the end of the experiments, urethane-anesthetized rats (1.5 g/kg) were prone positioned to obtain uninterrupted ECG recordings using noninvasive computerized ECG apparatus from. Kent Scientific (USA). Heart rate and ECG components including ST segment, wave. QT, P-R and R-R intervals, and QRS complex were electronically measured.

Sample Collection and Heart to Body Ratio Measurement

Subsequent to ECG determination, blood samples were collected and the hearts were directly removed and balanced using an animal weighing scale prior to storage. The obtained blood samples were centrifuged and the serum from different experimental groups was frozen in −80° C. for further biochemical examinations.

Infarct Size Determination

Frozen hearts were cut into 4-5 transverse incubated in 10% TTC (dissolved phosphate buffer, pH 7.4) for 25 min. at room temperature, fixed using 10% formaldehyde, and finally quantified using Image J® program (National Institutes of Health, University of Wisconsin).

Assessment of Biochemical Parameters

The extracted heart tissues were homogenated in 10% phosphate buffer to be used for the measurement of numerous biochemical parameters, including cardiac enzymes, apoptotic markers, inflammatory mediators' markers, and total protein. ELISA kits were consumed to measure cardiac enzymes: CPK, CK-MB, cTnT, and cTnI; apoptotic markers: Caspase 3 and Caspase 9 and inflammatory mediators: TNF-α, IL-1β, and NFκB. All ELISA Kits were used according to the manufacturer's protocols and using a microplate reader SpectraMax i.3× (Molecular Devices, USA).

Quantitative Analysis of TLR Pathway

Real-time PCR was preformed according to known techniques. Primer sequences used in this study were as follows: Bcl-2-F:5'-CCGGGAGATCGTGATGAAGT-3'(SEQ ID NO: 1), Bcl-2-R:5'-ATCCAGCC TCCGTTATCCT-3' (SEQ ID NO:2), Bax-F:5'-GTGGTTGCCCTCTTC-TACTTTG-3'(SEQ ID NO: 3), Bax-R: 5'-CA CAAA-GATGGTCACTGTCTGC-3' (SEQ ID NO: 4), TLR4-F:5'-AGTGTATCGGTGGTCAGTGTG CT-3' (SEQ ID NO: 5), TLR4-R:5'-AAACTCCAGCCACACATTCC-3' (SEQ ID NO: 6), TLR2-F: 5'-AAACT GTGT TCGTGCTTTCTGA-3' (SEQ ID NO: 7), TLR2-R:5'-CTTTCTTCTCAATGGGTT CCAG-3' (SEQ ID NO: 8), MyD88 -F:5'-GAGATCCGCGAGTTTGAGAC-3' (SEQ ID NO: 9), MyD88-R:5'-CTGTTT CTGCTGGT TG CGTA-3'(SEQ ID NO: 10), TRIF-F:5'-TCAGCCATTCTCCGTCCTCTTC-3' (SEQ ID NO: 11), TRIF-R:5'-GGTCAGC AGAAGGA-TAAGGAA-3' (SEQ ID NO: 12), β-actin-F:5'-TGACAG-GATGCAGAAGGAGA-3'(SEQ ID NO: 13), β-actin-R:5'-TAGAGCCACCAATCCACACA-3' (SEQ ID NO: 14).

For detection of the Toll-Like Receptors pathway protein expressions, Western blot was performed according to known methods.

Values were mentioned as mean SEM (n=6). Densitometry inquiry was accomplished via Image software for Western analysis. Statistical analysis appraisal was done via GraphPad Prism 5. Value p of <0.05 was considered statistically significant using one-way analysis of variance (ANOVA) followed by Tukey's test.

Example 1

Heart to Body Ratio Ward Size

Figure 1B:
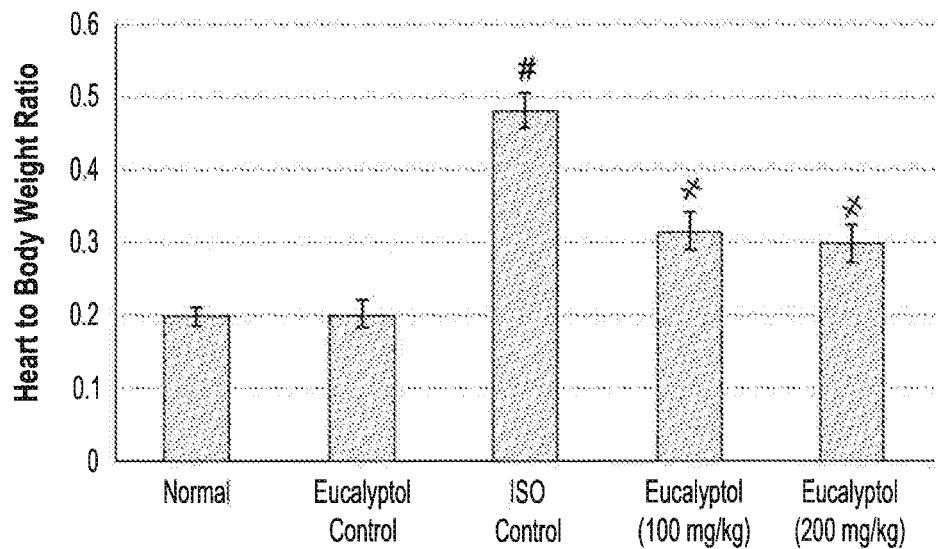
Figure 1C:
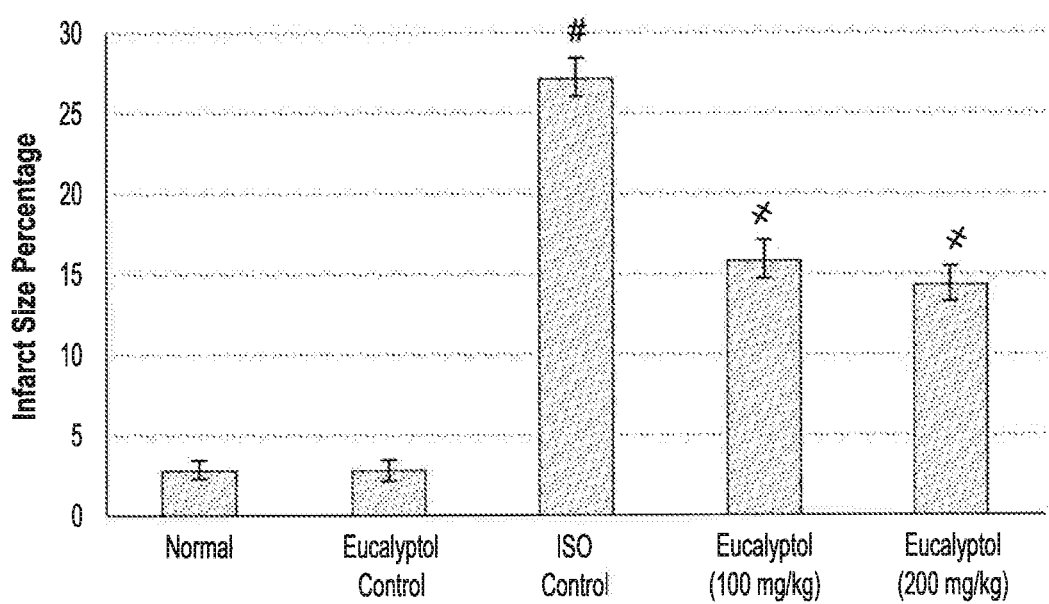
Figure 3A:
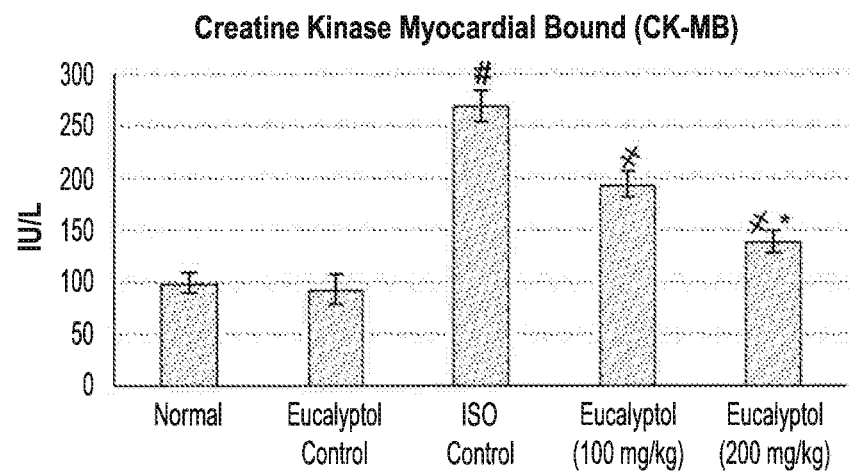
FIGS. 3A-3D are graphs showing the effect of pretreatment with eucalyptol (100 and 200 mg/kg) for 21 days on (A) CK-MB, (B) CPK, (C) cTnT and (p) cTnI in ISO induced MI animals. All values are stated as mean SD (n=6). Probability value is $p<0.05$: where # indicates statistically significant from normal control group, ≠ indicates statistically significant from ISO induced MI group, * indicates statistically significant from eucalyptol (100 mg/kg) group using one-way ANOVA followed by Tukey's test as a post-hoc analysis.
Figure 3B:
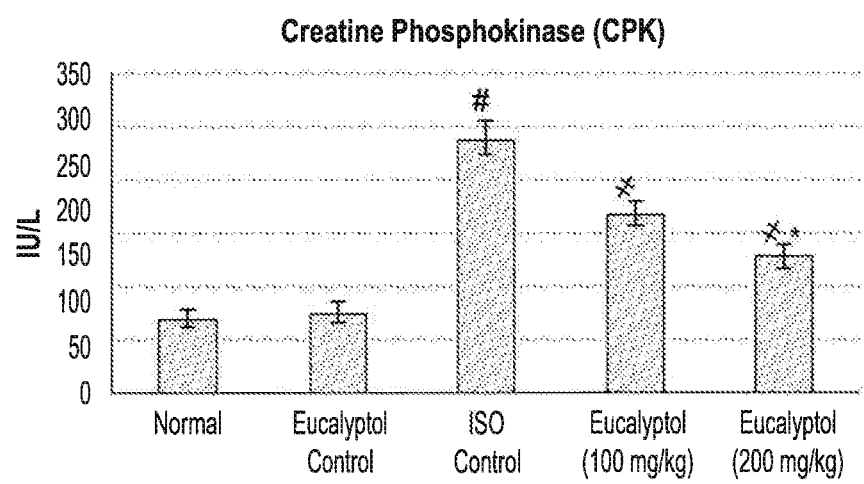
Figure 3C:
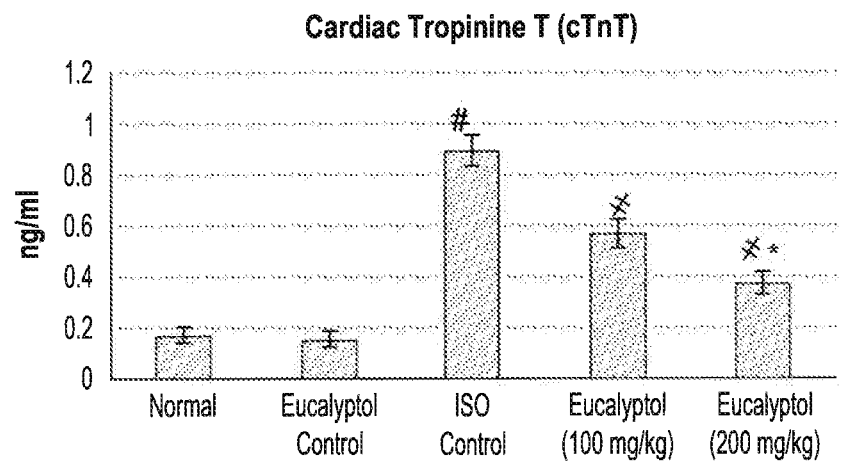
Figure 3D:
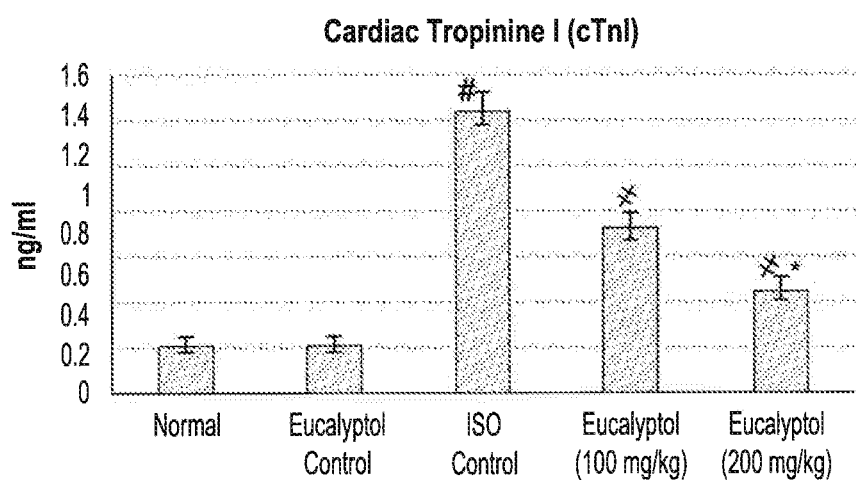
Figure 4A:
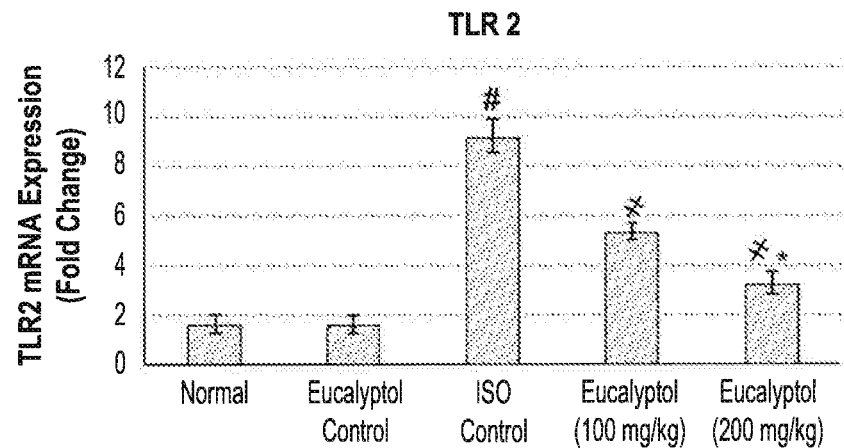
Figure 4B:
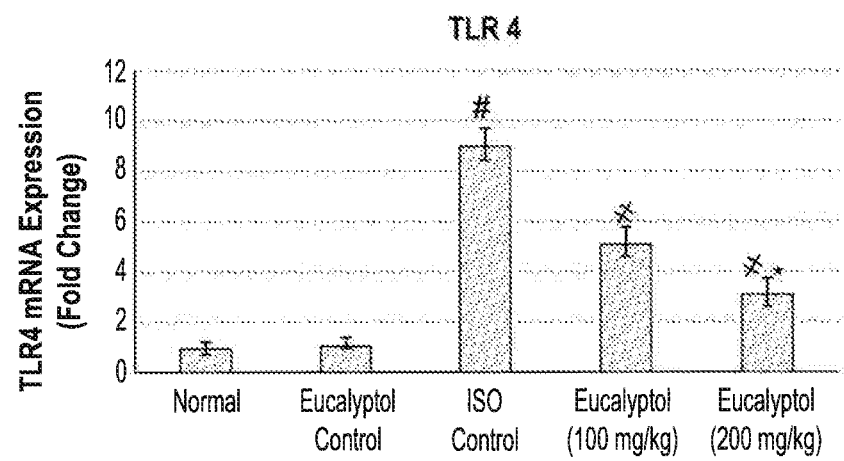
Figure 4C:
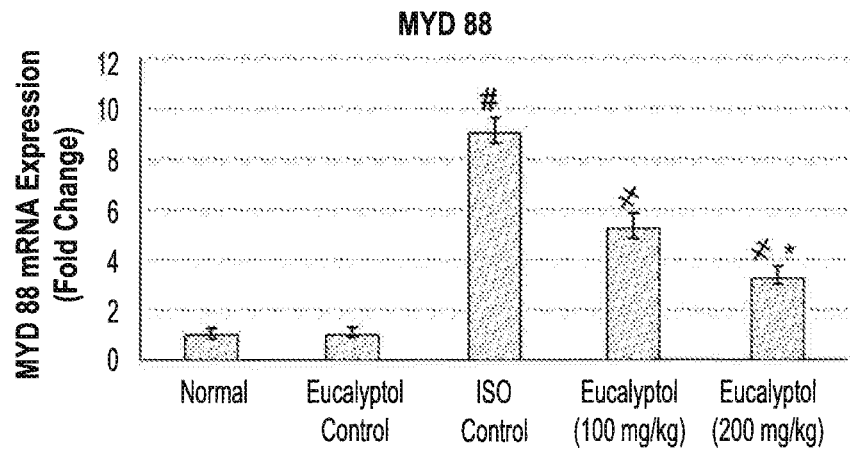
Figure 4D:
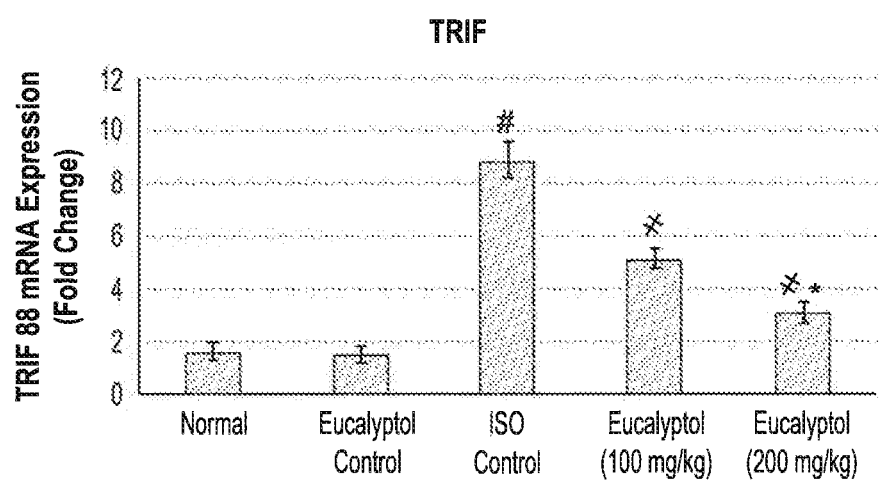
Figure 5A:
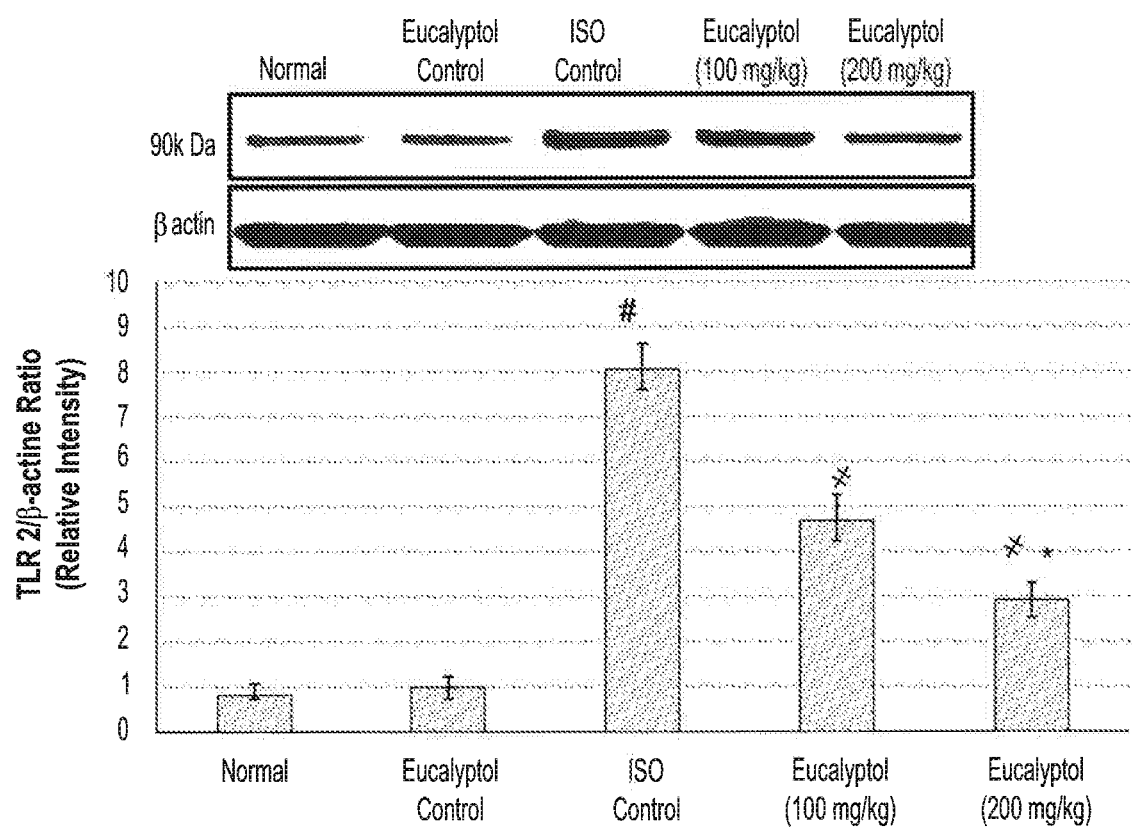
FIGS. 5A-5D are graphs the showing effect of pretreatment with eucalyptol (100 and 200 mg/kg) for 21 days on mRNA expression of (A) TLR 2, (B) TLR 4, (C) MYD 88 and (D) TRIF in ISO induced MI animals. All values were stated as mean±SD (n=6). Probability value is $p<0.05$: where # indicates statistically significant from normal control group, ≠ indicates statistically significant from ISO induced MI group, * indicates statistically significant from Eucalyptol (100 mg/kg) group using one-way ANOVA followed by Tukey's test as a post-hoc analysis.
Figure 5B:
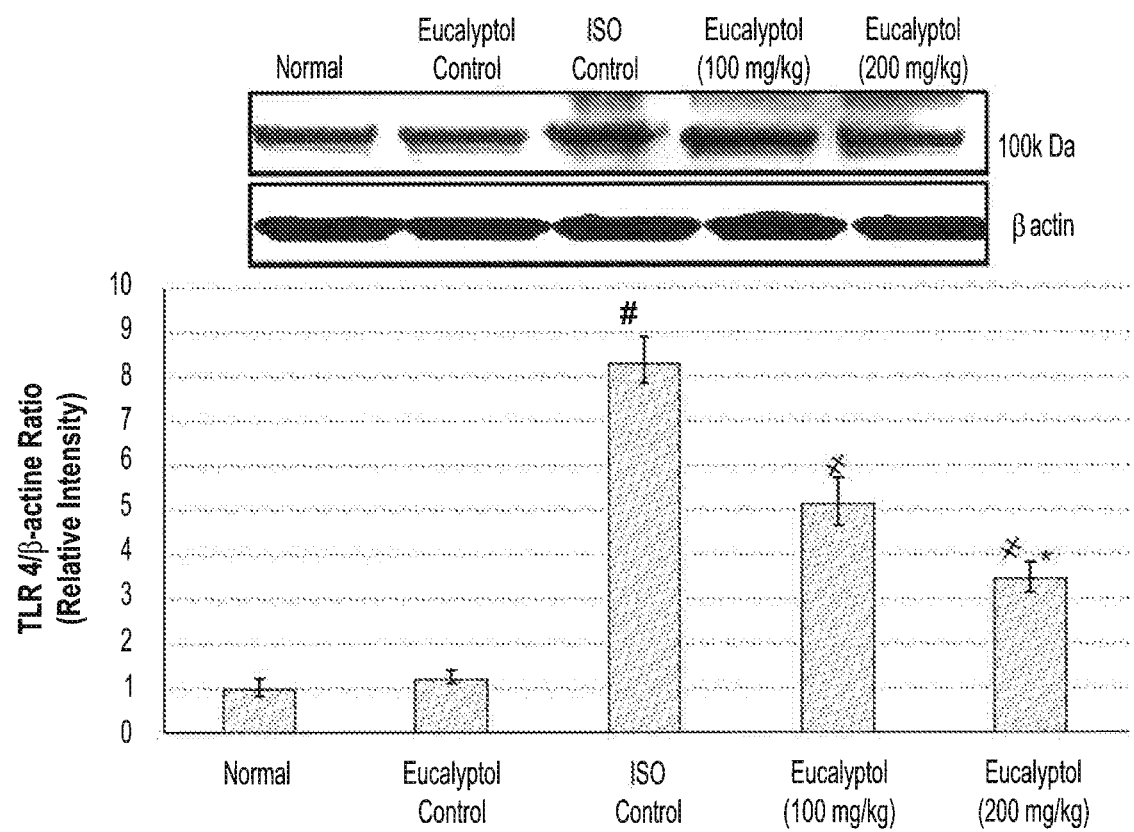
Figure 5C:
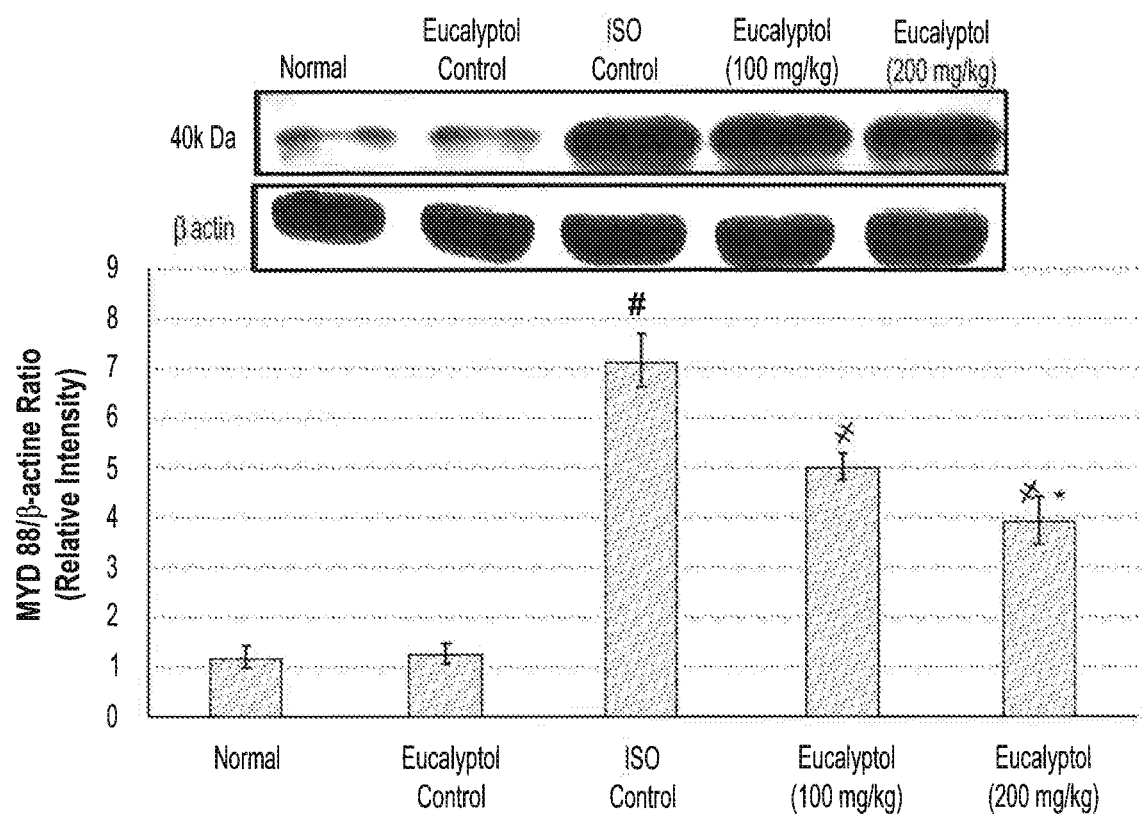
Figure 5D:
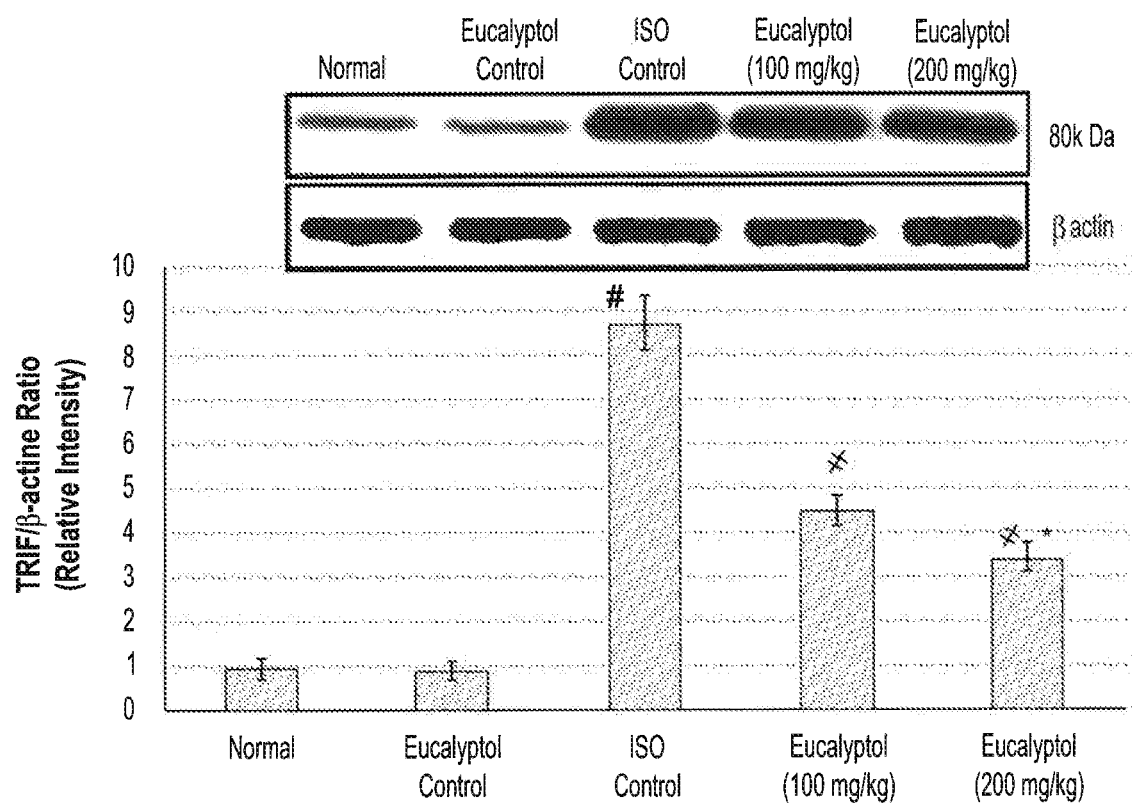
Figure 6A:
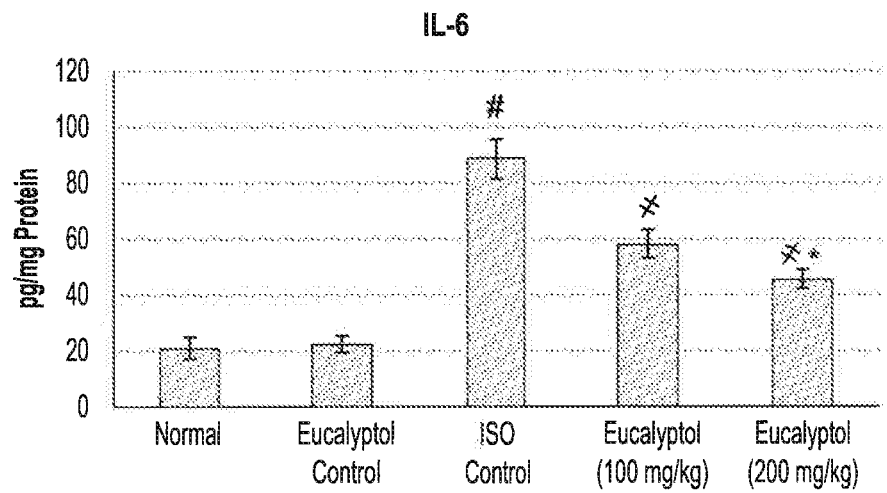
Figure 6B:
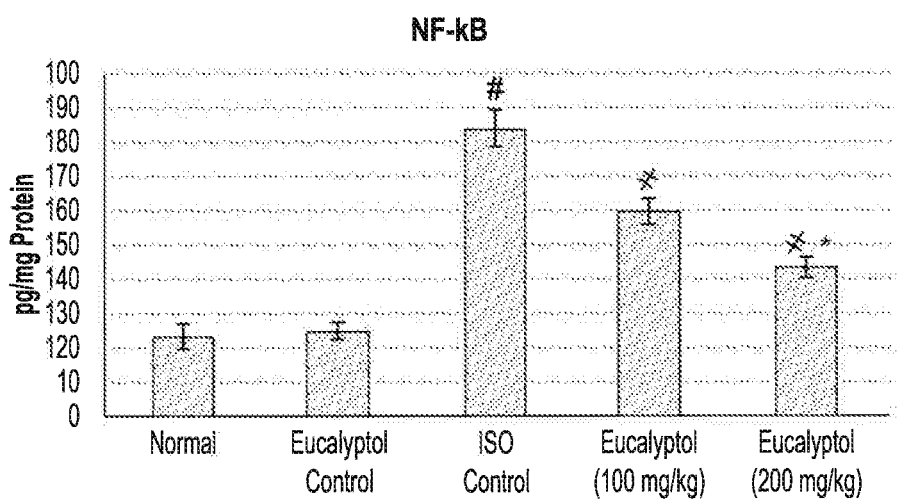
Figure 6C:
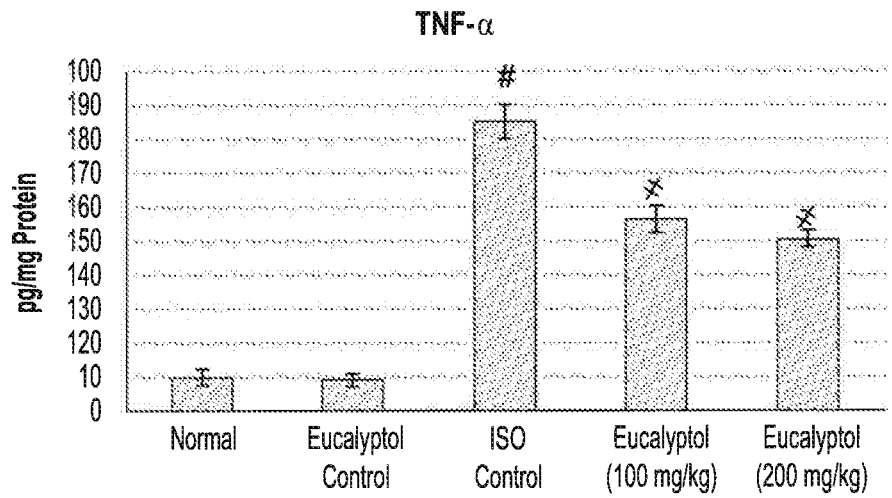
Figure 6D:
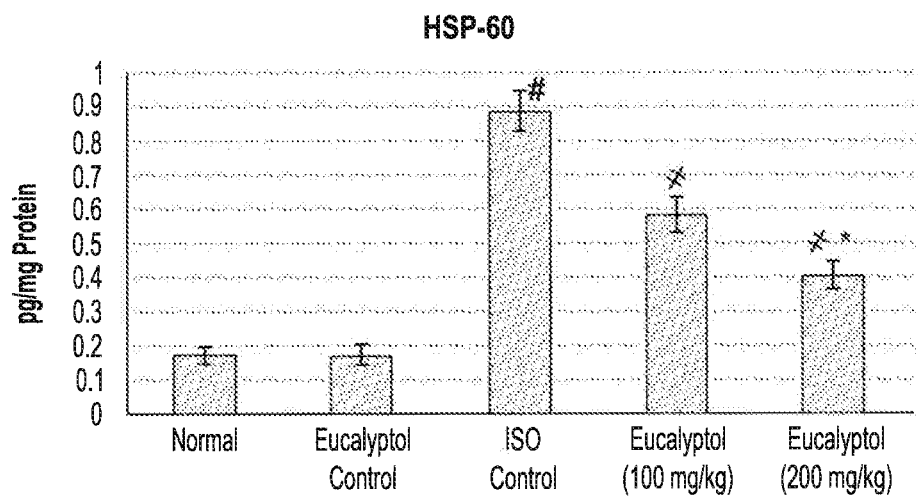
Figure 7A:
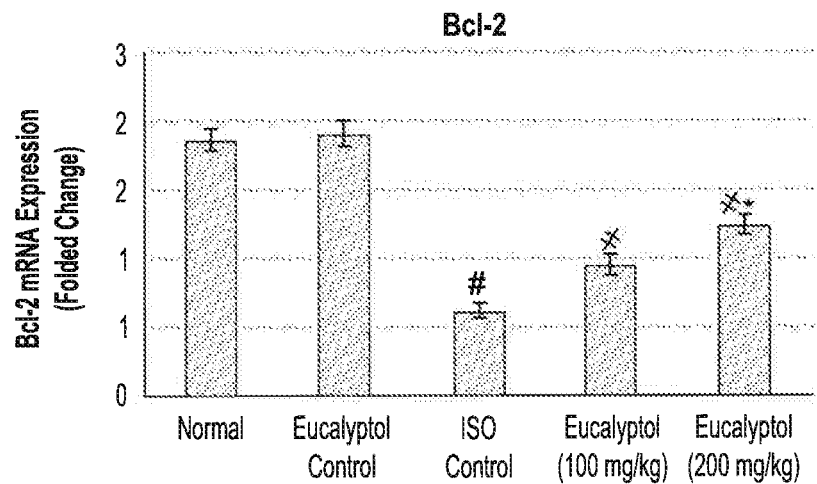
FIGS. 7A-7D are graphs showing the effect of pretreatment with eucalyptol (100 and 200 mg/kg) for 21 days on (A) Bcl-2 mRNA expression, (B) Bax mRNA expression, (C) Caspase 3 and (D) Caspase 9 in ISO induced MI animals. All values were stated as mean±SD (n=6). Probability value is $p<0.05$: where # indicates statistically significant from normal control group, ≠ indicates statistically significant from ISO induced MI group, * indicates statistically significant from Eucalyptol (100 mg/kg) group using one-way ANOVA followed by Tukey's test as a post-hoc analysis.
Figure 7B:
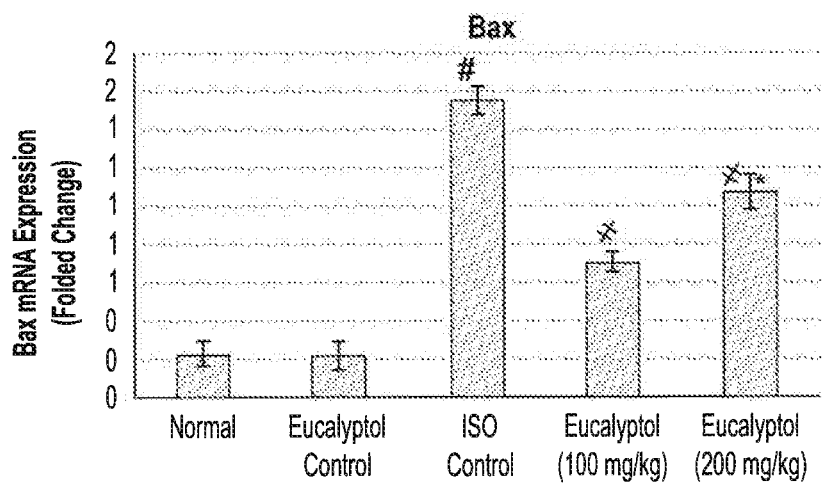
Figure 7C:
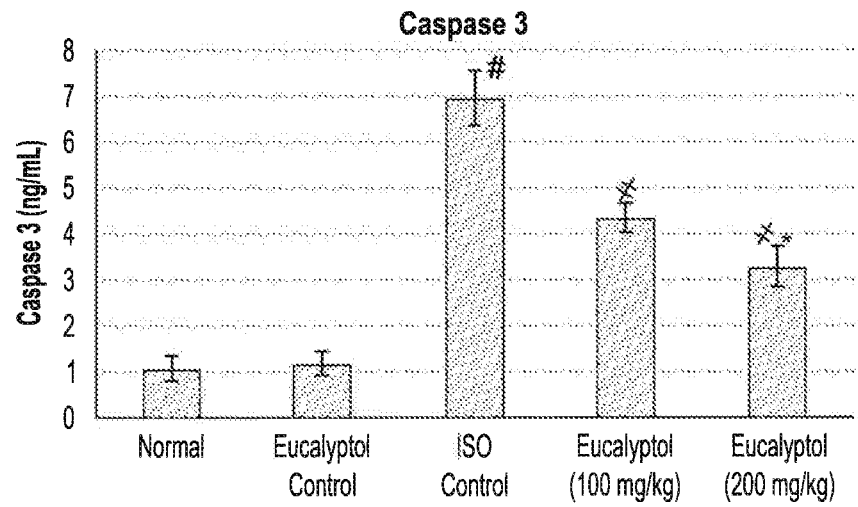
Figure 7D:
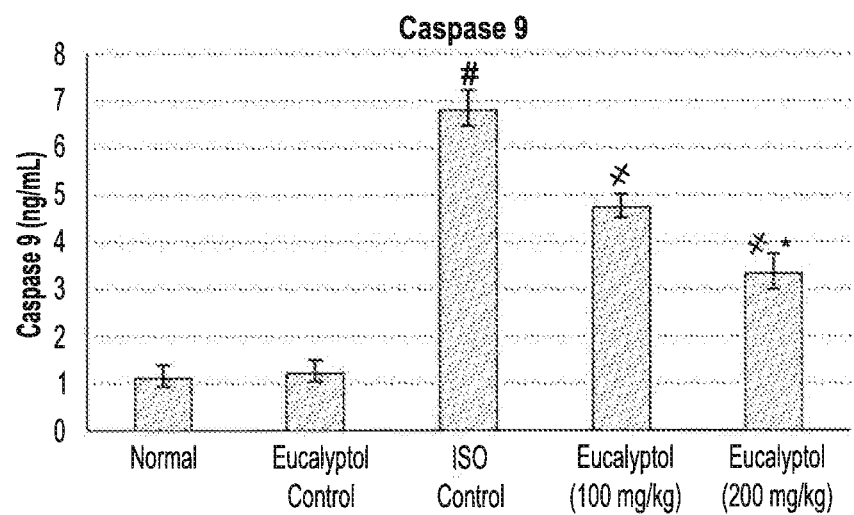

TTC stained heart slices were taken from normal, eucalyptol control, and the different ISO induced MI experimental animal groups, to determine effect on heart to body ratios (FIG. 1B) and infarcted area magnitude (FIG. 1C). The MI group (without pretreatment with eucalyptol) revealed significant (p<0.05) increase in heart to body ratio together with an upsurge in infarcted regions. On the other hand, pretreatment with Eucalyptol (100, 200 mg/kg) showed significant infarcted restricting action.

Example 2

Heart Rate and Electrocardiographic Traces

Normal and eucalyptol control groups presented normal heart rate (FIR) and electrocardiographic (ECG) patterns, whereas ISO induced MI showed a substantial intensification in FIR as well as numerous ECG alterations, including ST segment and QT interval widening, shortening in P wave, QRS complex, and P-R and R-R intervals compared with control groups. Table 1 shows the effect of pretreatment with eucalyptol (100, 200 mg/kg) for 21 days on heart rate and ECG components in ISO-induced myocardial infarction. As shown in Table 1 and depicted in FIGS. 2A-2D, pretreatment with eucalyptol (100, 200 mg/kg) reversed HR as well as ECO alterations.

expression of TLR pathway, FIGS. 5A-5D. Normal and eucalyptol control groups displayed no effect on the TLR pathway protein content. Animals experiencing MI exhibited a significant ($p<0.05$) proliferation in the protein expression of TLR 2, TLR 4, MyD 88, and TRIF. Pretreatment with Eucalyptol at doses of 100 and 200 mg/kg lessened post-

TABLE 1

Effects on Heart Rate and ECG Components in ISO-induced Myocardial Infarction after Pretreatment with Eucalyptol (100, 200 mg/kg) for 21 days

|  | Normal | Eucalyptol control | ISO control | Eucalyptol (100 mg/kg) | Eucalyptol (200 mg/kg) |
|---|---|---|---|---|---|
| Heart Rate (beat/min) | 375 ± 55.70 | 398.16 ± 43.67 | 213.3 ± 21.22 # | 294 ± 21.06 ≠ | 337.16 ± 14.98 ≠ |
| ST segment (mV) | 0.027 ± 0.002 | 0.025 ± 0.002 | 0.184 ± 0.013 # | 0.061 ± 0.009 ≠ | 0.046 ± 0.009 ≠ |
| P Wave (sec.) | 0.019 ± 0.003 | 0.019 ± 0.002 | 0.005 ± 0.001 # | 0.015 ± 0.001 ≠ | 0.015 ± 0.001 ≠ |
| QRS complex (sec.) | 0.042 ± 0.001 | 0.042 ± 0.001 | 0.029 ± 0.001 # | 0.038 ± 0.001 ≠ | 0.035 ± 0.001 ≠ |
| QT interval (sec.) | 0.045 ± 0.004 | 0.047 ± 0.002 | 0.081 ± 0.003 # | 0.064 ± 0.003 ≠ | 0.061 ± 0.003 ≠ |
| P-R interval (sec.) | 0.232 ± 0.023 | 0.230 ± 0.012 | 0.160 ± 0.003 # | 0.212 ± 0.012 ≠ | 0.222 ± 0.05 ≠ |
| R-R interval (sec.) | 0.230 ± 0.031 | 0.222 ± 0.012 | 0.145 ± 0.002 # | 0.180 ± 0.004 ≠ | 0.183 ± 0.056 ≠ |

All values were stated as mean ± SD (n = 6). Probability value is $p < 0.05$: where # indicates statistically significant from normal control group, ≠ indicates statistically significant from ISO induced MI group, @ indicates statistically significant from Eucalyptol (100 mg/kg) group using one-way ANOVA followed by Tukey's test as a post-hoc analysis.

Example 3

Eucalyptol Effects on Cardiac Enzymes

Normal and eucalyptol control groups exhibited normal cardiac enzymes including Creatine Phosphokinase (CPK), Creatine Kinase Myocardial Bound (CK-MB), Cardiac Tropinine T (cTnT) and Cardiac Tropinine I (cTnI), whereas ISO induced MI group showed a substantial intensification in cardiac enzymes compared to control groups. Pretreatment with Eucalyptol (100, 200 mg/kg) significantly diminished these cardiac enzymes as shown in FIGS. 3A-3D.

Example 4

Eucalyptol Effects on the TLR Pathway (TLR 2, TLR 4, MYD 88, and TRIF) mRNA Expression Levels Real-time quantitative PCR outcomes demonstrated that animals suffering from MI induced via ISO exhibited a considerably increased expression of TLR 2, TLR 4 as well as their adaptor proteins MYD 88, and TRIF, as presented in FIGS. 4A-4D. Pretreatment with eucalyptol (100, 200 mg/kg) considerably ($p<0.05$) declined TLR 2, TLR 4, MYD 88 and TRIF relative expression levels when related to ISO induced MI control group (FIGS. 4A-4D).

Example 5

Eucalyptol Effects on the Protein Expression of TLR Pathway (TLR 2, TLR 4, MYD 88, and TRIF)

TLR pathway, specifically TLR 2, TLR 4, MYD 88, and TRIF protein expression were evaluated via Western blot in the cardiac tissue obtained from the different experimental groups to identify the effect of eucalyptol on the protein myocardial infarction intensification of TLR pathway protein expression, FIGS. 5A-5D.

Example 6

Eucalyptol Effects on Heat Shock Protein (HSP-60) and Inflammatory Mediators

Normal and eucalyptol control groups displayed no effect on HSP-60 and inflammatory markers (TNF-α, IL-6 and NFκB) while myocardial infarction caused a significant ($p<0.05$) elevation in HSP-60 and inflammatory marker levels. Pretreatment with eucalyptol at doses of 100 and 200 mg/kg diminished myocardial infarction elevation in inflammatory mediators and HSP 60 as a DAMP molecule, FIGS. 6A-6D. Eucalyptol in a dose of 200 mg/kg caused a further significant reduction in HSP-60 IL-6 and NFκB than 100 mg/kg except for TNF-α in which a non-significant difference was found between both doses, FIGS. 6A-6D.

Example 7

Eucalyptol Effects on Apoptotic Status within the Myocardium

Normal and eucalyptol control groups displayed no effect on Bax, Bcl2, Caspase 3 and 9. Bax mRNA expression level and Caspase 3 and 9 activities were significantly amplified, while Bcl-2 mRNA expression was remarkably inferior in MI animals ($p<0.05$), demonstrating an apoptotic status ascending within the myocardium of MI animals, FIG. 7. However, the pretreatment of animals with eucalyptol, deteriorated Bax relative mRNA expression and Caspase 3 and 9 activities, while Bcl-2 was intensified, indicating that eucalyptol may limit MI induced myocardial apoptosis, FIG. 7.

It is to be understood that the present method is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of treating myocardial infarction in a patient having an increased level of at least at least one protein selected from the group consisting of TLR2, TLR4, MyD88, and TRIF comprising:
   (1) identifying the patient having an increased level of at least at least one protein selected from the group consisting of TLR2, TLR4, MyD88 and TRIF; and
   (2) administering a therapeutically effective amount of eucalyptol to the patient, wherein the therapeutically effective amount is selected from the group consisting of 100 mg/kg daily and 200 mg/kg daily and wherein the therapeutically effective amount of eucalyptol inhibits expression of at least one protein selected from the group consisting of TLR2, TLR4, MyD88, and TRIF.

2. The method of claim 1, wherein the eucalyptol is isolated from the essential oil of a *eucalyptus* plant.

3. The method of claim 1, wherein the eucalyptol is administered orally.

4. A method of treating myocardial infarction in a patient having an increased level of at least at least one protein selected from the group consisting of TLR2, TLR4, MyD88, and TRIF comprising:
   (1) identifying the patient having an increased level of at least at least one protein selected from the group consisting of TLR2, TLR4, MyD88, and TRIF; and
   (2) administering a pharmaceutical composition to the patient, the pharmaceutical composition consisting essentially of a therapeutically effective amount of eucalyptol and a pharmaceutically acceptable carrier, wherein the therapeutically effective amount comprising a dosage of eucalyptol selected from the group consisting of 100 mg/kg daily and 200 mg/kg daily and wherein the therapeutically effective amount of eucalyptol inhibits expression of at least one protein selected from the group consisting of TLR2, TLR4, MyD88,_and TRIF.

5. The method of claim 4, wherein the eucalyptol is isolated from the essential oil of a *eucalyptus* plant.

6. The method of claim 4, wherein the eucalyptol is administered orally.

* * * * *

```
                              SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ccgggagatc gtgatgaagt                                                   20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
atcccagcct ccgttatcct                                                   20

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
gtggttgccc tcttctactt tg                                                22

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
caaagatggt cactgtctgc                                                   20

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
agtgtatcgg tggtcagtgt g                                                 21

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
aaactccagc cacacattcc                                                   20
```

```
<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
aaactgtgtt cgtgctttct ga                                              22

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
ctttcttctc aatgggttcc ag                                              22

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
gagatccgcg agtttgagac                                                 20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ctgtttctgc tggttgcgta                                                 20

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
tcagccattc tccgtcctct tc                                              22

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
ggtcagcaga aggataagga a                                               21

<210> SEQ ID NO 13
<211> LENGTH: 20
<212> TYPE: DNA
<213> ORGANISM: Artificial Sequence
<220> FEATURE:
```

```
<223> OTHER INFORMATION: Primer

<400> SEQUENCE: 13
tgacaggatg cagaaggaga                                          20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tagagccacc aatccacaca                                          20
```